United States Patent
Kettunen et al.

(10) Patent No.: US 7,460,901 B2
(45) Date of Patent: Dec. 2, 2008

(54) PROCEDURE FOR DERIVING RELIABLE INFORMATION ON RESPIRATORY ACTIVITY FROM HEART PERIOD MEASUREMENT

(75) Inventors: Joni Kettunen, Saynatsalo (FI); Sami Saalasti, Jyvaskyla (FI)

(73) Assignee: Firstbeat Technologies Oy, Jyvaskyla (FI)

(*) Notice: Subject to any disclaimer, the term of this patent is extended or adjusted under 35 U.S.C. 154(b) by 490 days.

(21) Appl. No.: 10/515,170

(22) PCT Filed: May 30, 2003

(86) PCT No.: PCT/FI03/00426

§ 371 (c)(1),
(2), (4) Date: Nov. 18, 2004

(87) PCT Pub. No.: WO03/099114

PCT Pub. Date: Dec. 4, 2003

(65) Prior Publication Data
US 2005/0209521 A1    Sep. 22, 2005

(30) Foreign Application Priority Data
May 29, 2002    (FI)    ................................. 20025029

(51) Int. Cl.
*A61B 5/02*    (2006.01)
*A61N 1/00*    (2006.01)
(52) U.S. Cl. ......................................... 600/513; 607/20
(58) Field of Classification Search ................. 600/508, 600/513, 529; 607/20
See application file for complete search history.

(56) References Cited

U.S. PATENT DOCUMENTS

| | | | | |
|---|---|---|---|---|
| 3,212,496 | A | * | 10/1965 | Preston ........................ 600/484 |
| 4,129,125 | A | * | 12/1978 | Lester et al. ................. 600/484 |
| 4,463,764 | A | * | 8/1984 | Anderson et al. ............ 600/538 |
| 5,105,354 | A | * | 4/1992 | Nishimura ................... 600/484 |
| 5,400,794 | A | * | 3/1995 | Gorman ....................... 600/508 |
| 5,713,367 | A | * | 2/1998 | Arnold et al. ................ 600/517 |
| 5,820,567 | A | * | 10/1998 | Mackie ........................ 600/509 |
| 5,853,364 | A | * | 12/1998 | Baker et al. ................. 600/300 |
| 5,902,250 | A | * | 5/1999 | Verrier et al. ............... 600/515 |
| 5,913,308 | A | | 6/1999 | Forbes et al. |
| 5,995,868 | A | * | 11/1999 | Dorfmeister et al. ........ 600/544 |
| 6,030,342 | A | * | 2/2000 | Amano et al. ............... 600/503 |
| 6,129,675 | A | | 10/2000 | Jay |

(Continued)

OTHER PUBLICATIONS

Moody, G.B. et al. "Derivation of respiratory signals from multi-lead ECGs". In: Computers in Cardiology, Linkoping, Sweden, Sep. 8-11, 1985. Washington, DC, USA: IEEE Comput. Soc. Press, USA, 1985, pp. 113-116, Inspec an: 2843728, ISBN 0-8186-8733-9, see the whole document.

(Continued)

*Primary Examiner*—George R Evanisko
*Assistant Examiner*—Joseph M Dietrich
(74) *Attorney, Agent, or Firm*—Fildes & Outland, P.C.

(57) ABSTRACT

The present invention describes a method of tracking minute ventilation from R-R intervals that are based on the acquisition of ECG signal. Sub-methods (RDF1), which are mainly based on heart rate variability, are used, wherein the respiratory frequency is determined from a pattern of rhythmic changes in heart beat data. The sub-methods (RDF1-n) are combined using an expert function, wherein each sub-method (RDF1-n) determines an estimate of the respiratory frequency.

16 Claims, 11 Drawing Sheets

U.S. PATENT DOCUMENTS

| | | |
|---|---|---|
| 6,415,174 B1 | 7/2002 | Bebehani et al. |
| 6,480,733 B1 * | 11/2002 | Turcott ........................ 600/509 |
| 2003/0055348 A1 * | 3/2003 | Chazal et al. ................ 600/509 |
| 2003/0163054 A1 * | 8/2003 | Dekker ........................ 600/502 |

OTHER PUBLICATIONS

Varanini, M. et al. "Adaptive filtering of ECG signal for deriving respiratory activity". In: Computers in Cardiology Proceedings. Chicago, IL, USA, Sep. 23-26, 1990. Los Alamitos, CA, USA: IEEE Comput. Soc. Press, USA, 1991, pp. 621-624, Inspec an: 4127881, ISBN 0-8186-2225-3, see the whole document.

Travaglini, A. et al. "Repiratory signal derived from eight-lead ECG". In: Computers in Cardiology, Cleveland, OH, USA: Sep. 13-16, 1998. New York, USA: IEEE, 1998, pp. 65-68, Inspec an: 6168923, ISBN 0-7803-5200-9, see the whole document.

* cited by examiner

Time in seconds

PROCEDURE FOR DERIVING RELIABLE INFORMATION ON RESPIRATORY ACTIVITY FROM HEART PERIOD MEASUREMENT

BACKGROUND OF THE INVENTION

1. Field of the Invention

The invention relates to a method for deriving reliable information on respiratory activity from the heart beat data, wherein a sub-method, which is based on a heart rate variability, is used, wherein the respiratory frequency is determined from a pattern of rhytmic changes in heart beat data. The present invention relates generally to the monitoring of physiological parameters, in particular to those that are aimed to describe autonomic nervous system function. More specifically, the invention relates to a system for deriving respiratory information on the basis of ECG-signal alone and without being forced to set up an external device for respiratory measurement.

2. Description of the Prior Art

Heart period is among the most commonly used parameters in physiological monitoring. The wide use of heart period is related, on the one hand, to the availability of electrocardiograph (ECG) acquisition devices for noninvasive monitoring and, on the other hand, to its central role in the autonomic nervous system function and sensitivity to several physiological states and conditions in both clinical and non-clinical settings. Heart period (or, its reciprocal heart rate) forms a basis for different types of analyses and may be defined as the series of intervals between consecutive QRS-waveforms in the ECG-signal (see FIG. 2).

The fact that heart period is a complex product of several physiological mechanisms poses a challenge to the use of heart period in applied contexts. This is especially the case within ambulatory measurement, that is, measurement that is performed within natural, free-living conditions, outside of controlled laboratory environment and protocols. However, the multidetermined nature of the heart period may also bring forth a derivation of additional physiological measures from the heart period signal by means of decomposing the heart period into separate components that have a physiological interpretation.

Heart rate variability (HRV) is a general term used for describing periodic changes in heart period [1]. The so-called high frequency (HF)-component of HRV has an approximate frequency range of 0.15-0.50 Hz and is generally accepted as being reflective of parasympathetic nervous system activity. The rhythmic changes in the heart period consist of accelerative and decelerative changes in heart period that are mediated by consecutive withdrawal and re-gain of parasympathetic inhibitory drive on the sinoatrial node of the heart. The inspiration and expiration phases of a breathing cycle are associated with accelerative and decelerative changes in the heart period. Accordingly, during steady conditions, a pattern of rhythmic changes may be observed in the breathing frequency of the heart period (see FIG. 3a). It has been shown that the amplitude of these rhythmic changes, the respiratory sinus arrhythmia (RSA), reflects a level of tonic parasympathetic activity and may be therefore regarded as a noninvasive index of parasympathetic outflow to the heart.

The association between the breathing frequency and heart period brings forth the description of respiratory period on the basis of rhythmic changes in heart period. Although the respiratory component of HRV is clear during relatively steady conditions (e.g., metronome paced breathing in the laboratory, as described in FIG. 3b), the identification and accuracy of the RSA frequency diminishes considerably whenever the heart period signal obtained during ambulatory monitoring includes nonstationary changes that occur in either the breathing cycle or HRV. FIGS. 4a -c demonstrate the complexity and nonstationarities of the heart period signal during non-controlled, ambulatory measurement.

It is generally acknowledged that nonstationarities are rather the rule than exception in cardiovascular dynamics. Although this is clearly the case for ambulatory monitoring, it is also of note that it often difficult to obtain full control even in the laboratory environment. The relationship between the RSA frequency and respiratory period may be inflated by several known and unknown sources of naturally occurring nonstationarities and inconsistencies in the cardiac activity and respiratory patterns.

Although breathing period may stay at relatively fixed levels during stable conditions, such as rest or different phases of sleep, fast changes are typical in the rate of respiration rate and a substantial change in the adjacent periods may unfold within a single breathing cycle. Thus, the respiratory period may show a three-fold increase from 3 s to 9 s within a single respiratory cycle. It is generally known that several incidents that evoke naturally during non-controlled measurement, such as movement and postural change, speech, physical exercise, stress and sleep apnea, may produce significant alterations in the respiratory patterns.

The derivation of information on respiratory activity on the basis of HRV and RSA is challenged by complex nonstationarities in the rhythmic heart period patterns. These physiological sources of inconsistencies may be separated into three main categories. First, the respiratory pattern of HRV may be overshadowed by phasic accelerative and decelerative heart period responses to both physical and mental incidents, such as postural change, motor control, cognitive stimulation, and emotional arousal. These incidents are frequent, unpredictable from a physiological point of view, may have great amplitude and are often located in the frequency bandwidth of respiratory control.

Second, blood pressure control imposes continuous rhythmic changes with a highly nonstationary amplitude component at approximately 0.10 Hz. The amplitude of this component is substantially larger than that of respiratory-coupled RSA, which imposes a challenge for differentiating long respiratory intervals from nonstationary changes in the so-called 0.10 Hz rhythm.

Third, the amplitude of both the RSA and 0.10 Hz rhythms are sensitive to changes in overall physiological state. For example, when compared to resting conditions (see FIG. 5a), the RSA amplitude may show almost complete disappearance during maximal exercise (FIG. 5b) and certain clinical conditions. This effect also may be induced by the infusion of atropine, which blocks the parasympathetic control of the sinoatrial node (FIG. 5c). The localization of respiratory period during periods of decreased RSA amplitude is not possible without very efficient signal-enhancing procedures for extracting physiologically valid information from the heart period.

In addition to these different forms of naturally occurring nonstationarities inherent in the physiological signal, there are also other forms of physiological relationships and dependencies that modulate the relationship between RSA and respiratory period, or decrease the signal-to-noise-ratio in other forms. For example, it is generally known that the amplitude of the respiratory period coupled heart period oscillations is modulated by the respiratory period. Accordingly, the amplitude of the RSA increases towards lower frequencies (<0.20 Hz). Furthermore, the fact that the respiratory coupled rhythm is not often exactly sinusoidal but may be composed of several periodic components at different phases of the respiratory cycle imposes inherent difficulties to the direct use of the standard signal processing algorithms in characterizing the periodic components of HRV.

It may be concluded from the above discussion that any attempt targeted at using heart period signal to describe respiratory patterns within ambulatory, or otherwise non-controlled measurement, has to deal with the dynamics of various physiological components. In other words, dynamic changes in the respiratory period may not be successfully detected with the current state of methodology in terms of accuracy and optimal temporal resolution.

Whereas the measurement of ECG is widely available to both non-clinical and clinical purposes and can be performed relatively noninvasively (e.g., heart rate monitors), the methodology for the measurement of respiration is typically more restricted in its use. The most common type of sensor for the measurement of respiratory period is a strain belt that is placed around the chest or abdomen. This method gives information on the respiratory period but is somewhat invasive in its use and also subject to artifacts whenever movement occurs. Another commonly used method is a spirometer that is connected to a mouthpiece. The advantage of this method is in its ability to monitor also tidal volume (i.e., respiratory depth) but it is highly invasive and is restricted to laboratory use only.

Whereas there have been numerous studies documenting the relationship between the frequency of the RSA component and the respiratory period, Prior Art has not documented any direct attempts of monitoring respiratory activity on the basis of heart period measurement alone. In a closely related field, Prior Art has documented a method of deriving respiratory information on tidal volume on the basis of blood pressure signal that has been derived from the implanted blood pressure sensor (U.S. Pat. No. 5,980,463, Brockway et al.). The work of Brockway et al. is based on a sensor that is implanted within the blood vessel and is only applicable to non-human subjects. The respiratory rhythm is then derived by a simple time domain fitting of nonlinear curve to the systolic and diastolic phases of the blood pressure oscillations. It is clear to one experienced in the art that the procedure presented by Brockway et al. is not suitable for the analysis of respiratory activity on the basis of heart beat data, since a heart beat signal contains considerably more noise and does not provide continuous measurement values as is the case for the blood pressure signal. Furthermore, the described method involves an implantation and, as described by Brockway et al., may be only applied to non-human subjects.

Following publications are referred herein. These disclose generally frequency and time frequency methods for versatile analyzing of heart rate variability.

Akselrod, S., Gordon, D., Ubel, F. A., Shannon, D. C., Barger, A. C., & Cohen, R. J. (1981). Power spectral analysis of heart rate fluctuation: A quantitative probe of beat-to-beat cardiovascular control. *Science*, 213, 220-222 [1].

Novak, P. & Novak, V. (1993). Time/frequency mapping of the heart rate, blood pressure and respiratory signals. *Medical and Biological Engineering and Computing*, 31, 103-110 [2].

Pistelli, F., Bottai, M., Viegel, G., Di Pede, F., Carrozzi, L., Baldacci, S., Pedreschi, M. & Giuntini, C. 2000. Smooth reference equations for slow vital capacity and flow-volume curve indexes. *American Journal of Respiratory and Critical Care Medicine*, 161, 899-905 [3].

Pola, S., Macerate, A., Emdin, M., & Marchesi, C. (1996). Estimation of the power spectral density in nonstationary cardiovascular time series: assessing the role of the time-frequency representations (TFR). *IEEE Transactions on Biomedical Engineering*, 43, 46-59 [4].

The work of Heikkilä (U.S. Pat. No. 5,810,722) has described an embodiment of respiratory information as a part of method determining threshold values for energy metabolism. Heikkilä bases this work on a simple filtering and time domain fitting of respiratory phases similar to that presented in Brockway. It is, however, quite clear to anyone working in the field that the method described by Heikkilä is not capable of tracking nonstationary changes in respiratory period or giving accurate information on respiratory period during conditions such as exercise, since the signal-to-noise properties of the RSA signal is rather poor in the time domain. Accordingly, the procedure described in Heikkilä may be justified in the context of providing information on the energy metabolism thresholds, but it clearly lacks the sophistication required for the reliable and accurate calculation of respiratory period from the heart period signal.

Prior Art has documented related work on the general use of time-frequency analysis to describe temporal fluctuations in HRV [2],[4]. There are several available methods to perform a time-frequency decomposition of time series data. The most common and relatively robust method is a short-term fast Fourier transformation, which is basically an ordinary fast Fourier transformation with a moving window. There are also other known methods for the analysis of the temporal changes in the frequency and amplitude characteristics of the heart beat data, including the smoothed pseudo-Wigner-Ville transformation that belongs to the Cohen's class of distributions, complex demodulation, and wavelet transformations. All of these methods have been earlier applied to analyze the frequency components of the HRV. Thus, these methods also have been used previously to describe the respiratory component of the HRV, but the methods are only descriptive as such and no solution has been reported on the automatic and artifact free identification of the respiratory period.

The derivation of minute ventilation (i.e., a measure of ventilation volume per minute) is the product of two components, respiratory period and tidal volume (i.e., the depth of breath). Accordingly, minute ventilation may be derived by using the following equation, Minute ventilation (1/min)=Respiratory rate (breaths/min)*Tidal volume (1/breath)

It is known in the prior art that the amplitude of the so-called respiratory sinus arrhythmia (RSA) of the heart period is also influenced by changes in tidal volume. This effect is based on mechanical influence of the lung volume changes on the cardiac nerves. This relationship has been widely documented in the literature. However, this relationship may be only observed under highly stationary and artificial conditions, since the major determinant of the amplitude of the respiratory sinus arrhythmia is the outflow of parasympathetic nervous system, the activity of which shows large variations across different physiological states.

There have been no solutions to the estimation of tidal volume on the basis of heart beat data only. One problem in such estimation is likely to arise from individual differences such as age, gender, height, and weight, which influence a person's vital capacity and therefore, lung volume. Pistelli [4] et al. have reported an example of an equation that may be used to estimate vital capacity on the basis of individual characteristics, which may be helpful in adjusting individual differences in the deepness of the breath.

The work of Heikkilä et al. (U.S. Pat. No. 5,810,722) may be referred to, wherein heart period has been used to provide information on tidal volume. The described method is based on the association between the heart rate level and tidal volume, and therefore, it is clear that the estimate of tidal volume is purely dependent on changes in heart rate level and produces false information on circumstances wherein changes in tidal volume are not associated with heart rate changes, which is most often the case. Moreover, estimates as provided by the described method are unitless and may provide information only on changes in tidal volume as a function of increased exercise intensity. To summarize, the work described in Heikkilä et al. is clearly designed for other purposes than providing exact information on tidal volume and thus, may not be used for such purposes.

A procedure of deriving respiratory frequency, tidal volume, and minute ventilation from the R-R signal would be highly useful in several areas of ECG- and heart rate monitoring by providing information on the respiratory activity without being forced to implement an external device for the detection of respiratory rhythm and ventilation volume. Such a procedure could be applied to many areas of clinical use (e.g., cardiac patients) and physiological monitoring (e.g., exercise, fitness, and health), wherein it is of interest to monitor and derive detailed information on the physiological state and characteristics of a subject.

SUMMARY OF THE INVENTION

The present innovation provides a procedure for determining respiratory period and ventilation computationally on the basis of ECG signal and therefore avoiding the need for setting up an external device for respiratory acquisition in connection with heart period measurement. Accordingly, a method for deriving reliable information on respiratory activity from the heart beat data, wherein a sub-method (RDF1), which is based on a heart rate variability, is used, wherein the respiratory frequency is determined from a pattern of rhythmic changes in heart beat data, is characterized in that at least one another sub-method (RDF2), which is based on a heart rate data, is used, and the said sub-methods (RDF1-n) are combined using an expert function, wherein each sub-method (RDF1-n) determines an estimate of the respiratory frequency.

The method may be characterized in that one sub-method (RDF1) is optimal for a steady condition or that at least one sub-method (RDF2) comprises determination of temporal changes in the respiratory frequencies by defining temporal deviations in the distribution of frequencies. A post-correction of the respiratory period may be made with a chosen method.

The method may be characterized in that an expert function comprises a reliability weightings for each sub-method as a function of the calculated respiratory frequency by the respective sub-method or that at least one sub-method (RDFi) is controlled dynamically according to the heart rate level.

The method may also be characterized in that the expert function makes a pre-selection from several different sub-methods (RDFn) with pre-selected criteria and that the expert function makes a fixed pre-selection for an implementation according to pre-measured empirical data.

Information on tidal volume may be calculated with the use of heart period and information on the ventilation from the heart beat data may be derived wherein the following methods (a-c) are used:
   a. The multiplication of heart beat derived values of tidal volume with heart beat derived values on the frequency of breathing,
   b. Applying information on at least one chosen parameter derived from the heart beat,
   c. Using a mathematical function to transfer the chosen parameters measures into information on ventilation.

The method may be used in a wearable computer or used in fitness exercise equipment.

Reliability of any estimate may be determined and expressed with the estimate.

A method of tracking respiratory information consists of following stages:
   (1) initial transformations of ECG and heart period,
   (2) filtering and time-frequency transformations,
   (3) extraction of computational features for respiratory period detection,
   (4) determination of respiratory frequency and its associated confidence interval for each time moment by combining several sources of information,
   (5) time domain correction and adjustment of the respiratory period signal,
   (6) estimation of tidal volume, and
   (7) computation of minute ventilation.

This innovation is highly useful as a key component in several apparatus aiming at describing human physiological function by proving information on respiratory activity without the requirement of introducing additional cost and difficulty to the installation of a measurement system that contains heart period measurement as an integral part.

The invented procedure of tracking respiratory information may be described as a dynamic expert system and consists of several computational stages: (1) initial transformations of ECG and heart period, (2) filtering and time-frequency transformations, (3) extraction of computational features for respiratory period detection, (4) determination of respiratory frequency and its associated confidence interval for each time moment by combining several sources of information, (5) time domain correction and adjustment of the respiratory period signal, (6) estimation of tidal volume, and (7) computation of minute ventilation. The presented procedure is capable of tracking short-term and long-term changes in the respiratory period and ventilation within the functional range of the respiratory system. The method has an excellent signal-to-noise ratio and a temporal sensitivity close to one respiratory cycle.

The invented procedure may be used to monitor both short-term and long-term changes in cardio respiratory function and may be applied to the analysis of off-line segments of data (post analysis of recorded data) or on-line data (real time analyzing e.g. in heart rate monitor). The procedure of respiratory detection and parasympathetic activity assessment may be optimized to fit certain specific conditions, such as normal life, clinically significant deviations from normal dynamics, and exercise, to obtain an optimal signal-to-noise ratio. The present innovation provides additional value to several domains of applications wherein noninvasive monitoring of physiological activity is relevant and ECG information can be obtained. Preferential areas of application include clinical use, health monitoring, and exercise monitoring and analysis.

The present innovation may be also used to provide a method of correcting for the respiratory artifact in the noninvasive estimation of parasympathetic activity. The information on respiratory period may be further applied to perform a frequency modulation of the quantified HRV power using special transfer function. This procedure provides both short-term and long-term respiratory adjusted indices of parasympathetic activity. This procedure may efficiently reduce respiratory induced artifacts in the HRV estimates and maybe therefore considered as an integral component of apparatus aiming at monitoring cardiac parasympathetic activity through HRV estimation.

These and other features and advantages of the invention will be more fully understood from the following detailed description of the invention taken together with the accompanying drawings.

DETAILED DESCRIPTION OF THE PREFERRED EMBODIMENTS

Introduction

The following terms and abbreviations are used herein:

Custom-designed filtering: The procedure of frequency modulating the amplitude of the HRV estimates using a filter that has been optimized for specific purpose.

Heart period (HP): The time period (ms) between consecutive R-peaks in the ECG waveform.

Heart rate variability (HRV): A general term for oscillatory periodic changes in the heart period. HRV may be further divided into high frequency (HF; 0.15-0.50 Hz), low frequency (LF; (0.04-0.15 Hz)), very-low frequency (VLF; 0.01-0.04 Hz) and ultra-low frequency (ULV; 0.0001-0.01 Hz) bands.

Instantaneous center frequency (ICF): The center of the mass in the (HRV) frequency distribution within a given time instant.

Maximum gradient: Maximum gradient is used to point the frequency location of maximum HRV amplitude within given time instant by finding the frequencies that have a sign change in the derivate from positive to negative. The maximum gradient is the gradient that has the maximum amplitude along the frequency dimension of the time-frequency transformation.

Respiratory detection feature (RDF). A parameter that describes the time-frequency distribution of R-R time series on a given time instant. Each RDF is associated with a specific custom-designed filter and a weighting factor that determines the use of RDF in the determination of the respiratory period.

Respiratory period (RP): The actual period of respiratory cycle as determined by the interval between consecutive initiation of inspiration or expiration phases.

Time-frequency distribution: The presentation of time domain data within a joint time-frequency distribution that has separate dimensions for time and frequency domains. The time frequency distribution may be obtained by using, for example, a short-term Fourier transformation (STFT) or smoothed-pseudo Wigner-Ville transformation (SPWV). Also complex demodulation and wavelet transform provide information on the frequency properties of the signal as a function of time.

The preferred embodiments of the invention are discussed in detail below. While specific configurations and arrangements are discussed, it should be clear that this is done for illustration purposes only. Accordingly, other configurations and arrangements may be used without departing from the spirit and scope of the invention.

Figure 1:
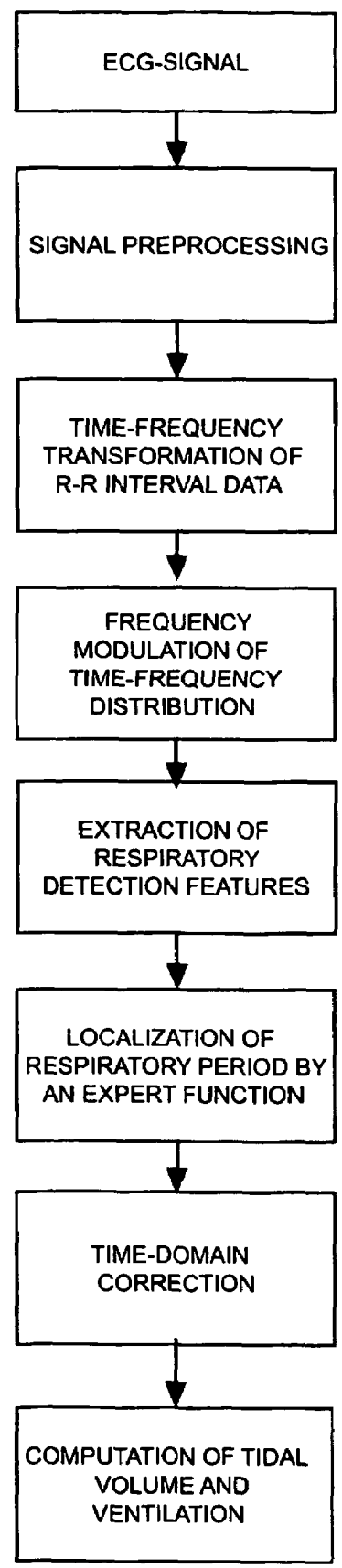
FIG. 1 shows the overall structure of the signal processing algorithms in the invention.
Figure 2:
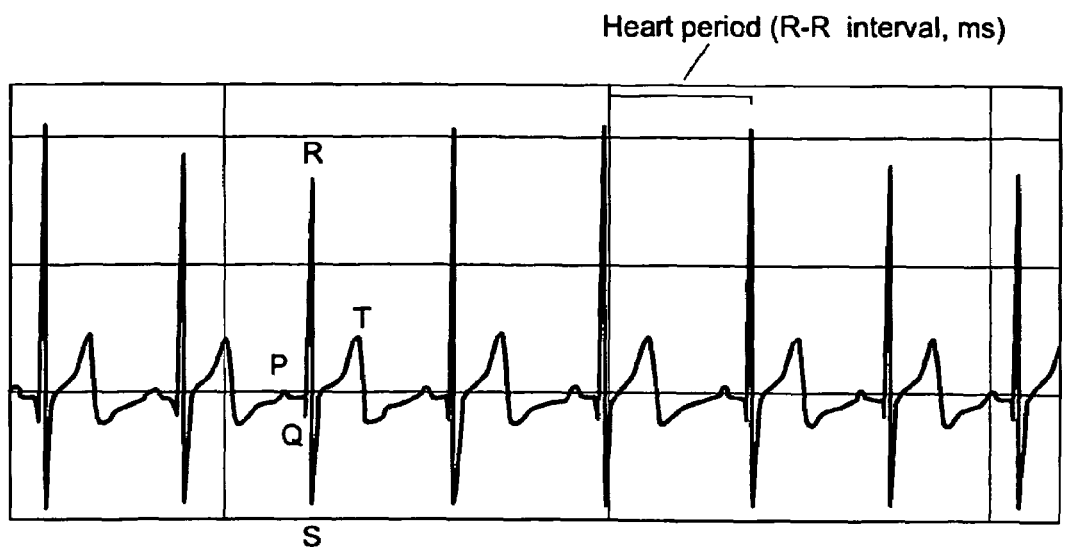
FIG. 2 shows a typical ECG signal with three QRS-waveforms and their intermediate R-R intervals.
Figure 3A:
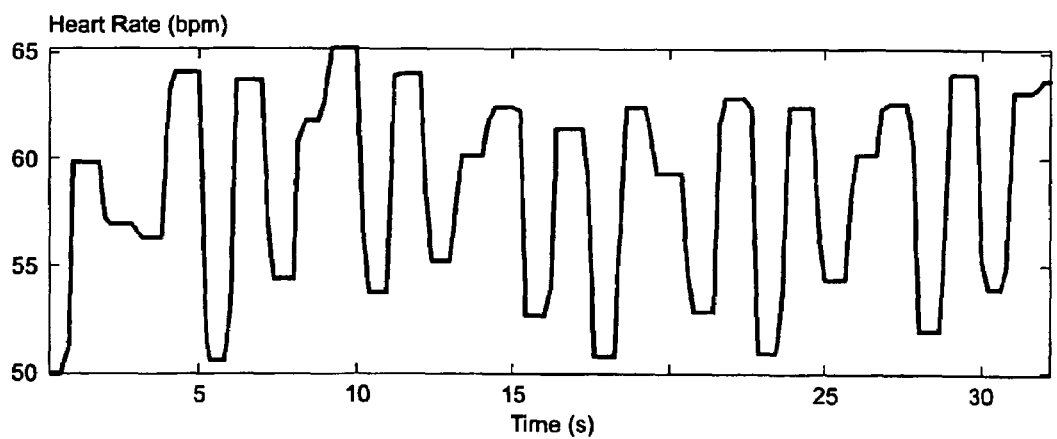
FIG. 3a is a plot of consecutive heart period data and respiration cycles illustrating the coupling of heart period and respiratory frequency during steady conditions.
Figure 3B:
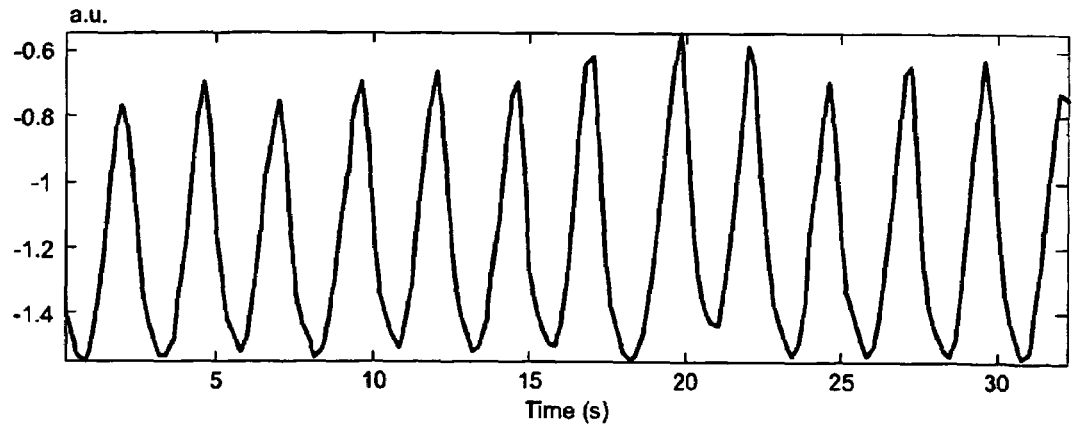
FIG. 3b illustrates the dynamic change in the frequency distribution of HRV during changes in the respiratory frequency.
Figure 4A:
FIGS. 4a, 4b and 4c illustrate the effects of nonstationary incidents, such as postural change and irregular breathing rhythms, on the heart period signal.
Figure 4B:
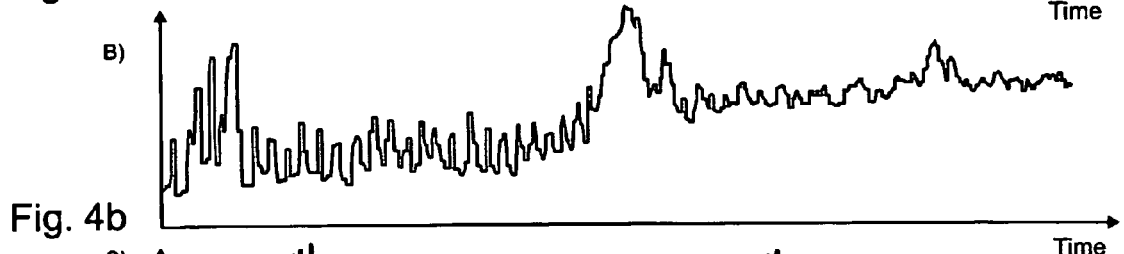
Figure 4C:
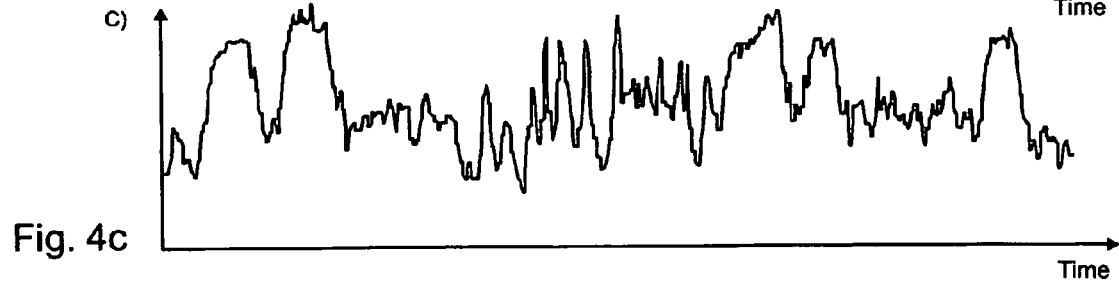
Figure 5A:
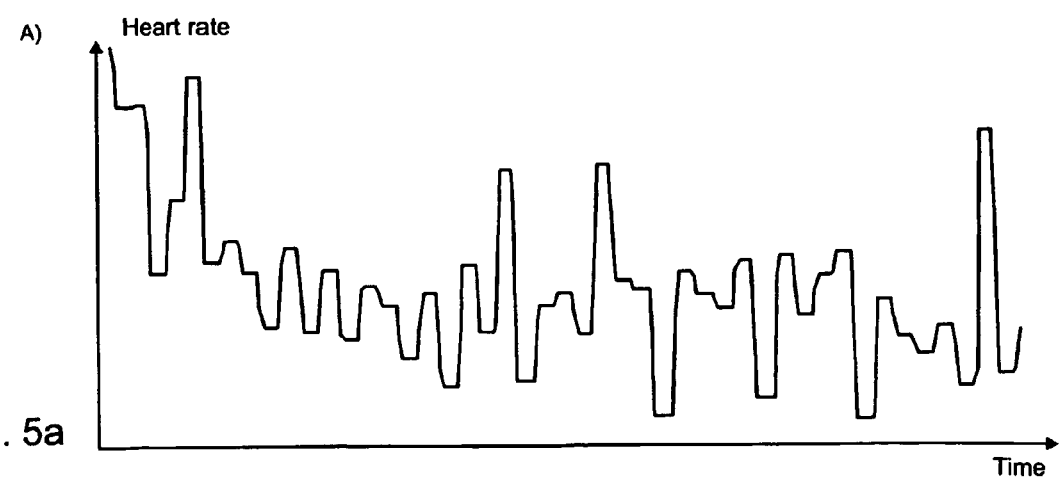
FIGS. 5a, 5b and 5c illustrate heart rate variability and especially the high-frequency component of it (A) at rest, (B) during physical exercise, and (C) after the injection of atropine.
Figure 5B:
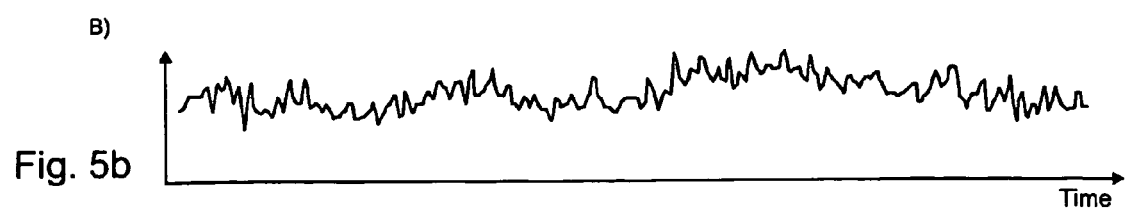
Figure 5C:
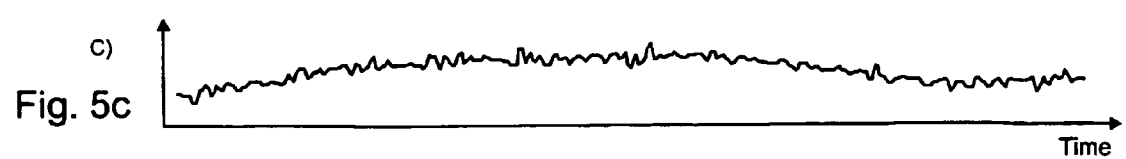
Figure 6:
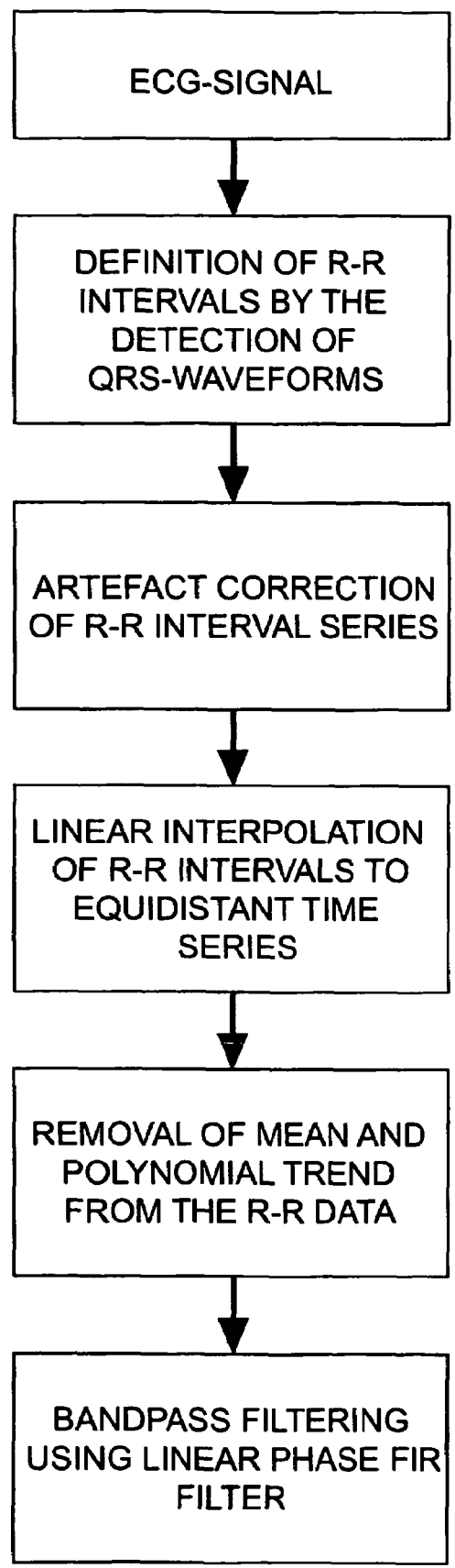
FIG. 6 presents a flow chart describing the preprocessing of the ECG signal.

FIG. 6 shows an overall view on the initial stages in the analysis of ECG-signal. FIG. 2 shows a typical record of ECG-signal and the transformation of ECG-signal into consecutive R-R intervals by using sequential QRS-complexes as markers of the beginning and end of a R-R interval. Also, other components of the ECG signal may be used to detect the R-R interval. The consecutive R-R intervals are scanned through an artifact detection filter to perform an initial correction of falsely detected, missed, and premature heart beats.

Consecutive artifact-corrected R-R intervals are transformed into equidistant heart period time series by using a weighted linear interpolation of the R-R intervals. For optimal results, a time domain sampling rate not less than 5 Hz is recommended. The sampling rate may be increased especially in order to gain better resolution for an occasion of rapid breathing rate (e.g., >1 Hz), as may be encountered in applications aiming at describing respiratory activity during intense exercise.

The heart period time series are detrended by subtracting the mean and a linear or a trend defined by a higher order polynomial from the heart period time series. A linear phase finite impulse response (FIR) filter with a band pass specified by the respiratory frequencies is performed to the detrended data. An optimal band pass width may be dependent on the applications of the respiratory data. For non-exercise applications in adults, a band pass of 0.04-1.00 Hz may produce optimal results, whereas for children and exercise applications higher frequencies may be needed. It is also recommended that special care is attended to the monitoring of nocturnal sleep wherein periods of very low breathing rate may be evident. It should be clear to one experienced in the art that the present implementation of filtering procedures is merely an example and different types of approaches may be used to obtain the same results.

Figure 7:
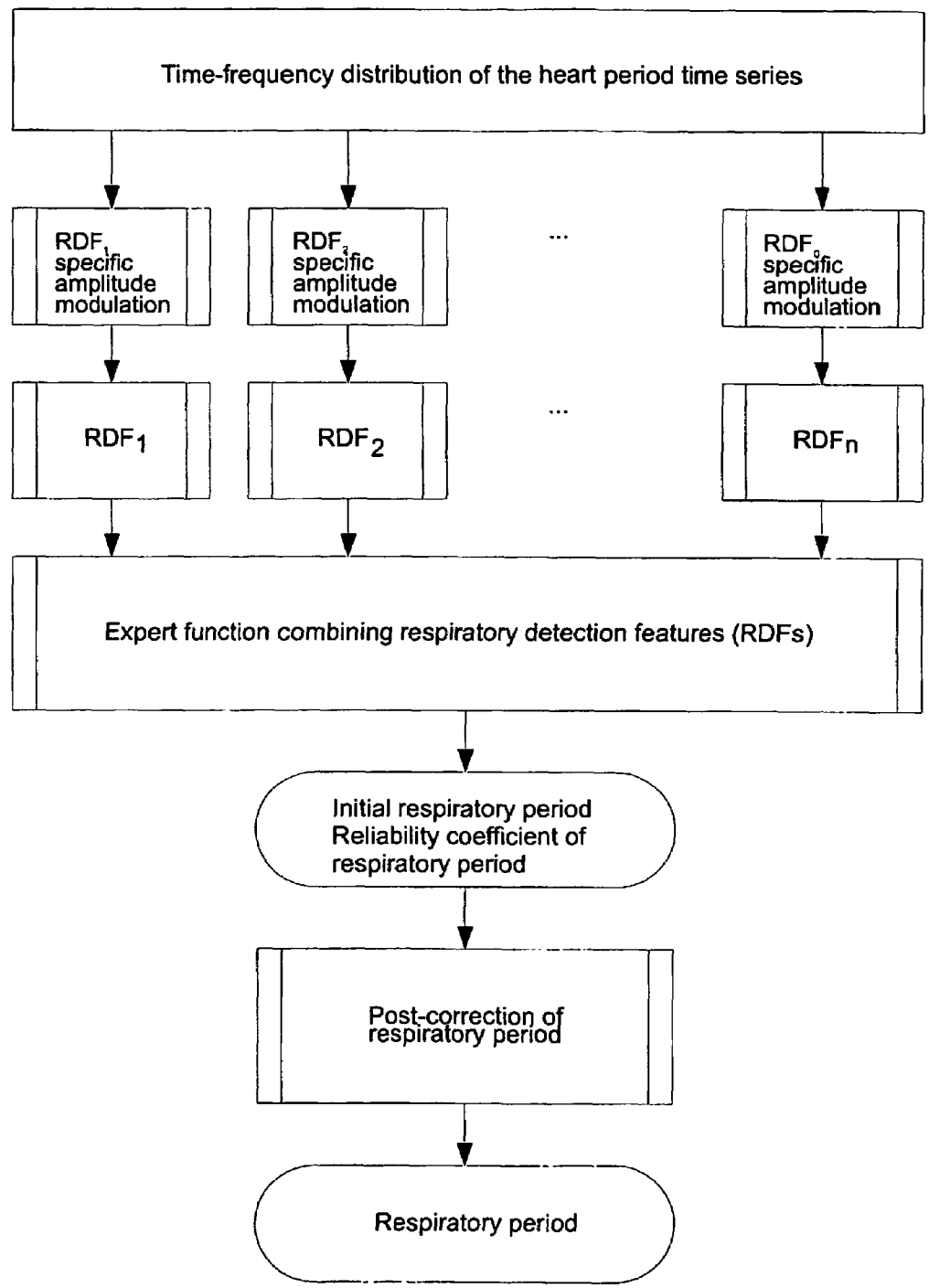
FIG. 7 presents a flowchart describing the extraction of respiratory detection features (RDFs) and the combination of the respiratory detection features in the expert function.

FIG. 7 presents the sequential steps and algorithms used in the extraction of respiratory detection features from the heart period data. The heart period data is transformed into time-frequency distribution by applying a time-frequency transformation. In this example all sub-methods use same time-frequency transformation, but many parameters could be varied. Thus, this stage with parameter variation could be a part of each sub-method. Generally there are two sub-methods if they differ from each other at least in one parameter at any computational stage. A preferred method of performing time-frequency transformation is short-term Fourier transformation (STFT), since it is computationally efficient and relatively robust. One possible temporal window for STFT is Hanning window of size 101, which equals to a window of 20 s within heart period data sampled to 5 Hz. Also another time-frequency transformations may be used. The use of smoothed pseudo Wigner-Ville distribution to perform the time-frequency transformation may provide better temporal accuracy but also suffices from cross-terms that bring inherent difficulties to the use of time-frequency transformed heart period data for the purposes of respiratory tracking. Other possible methods are, for example, complex demodulation and wavelet transformation, both of which may be used to provide temporal information on the frequency properties of the HRV. It is of course possible to compose the present innovation by using, instead of a continuous time-frequency distribution, a series of independent Fourier or other types of spectral profiles, which would provide a similar continuous spectra to those of time-frequency distributions.

Time-frequency transformed R-R data is prepared for the extraction of respiratory detection features (RDFs) by setting up amplitude modulation of time-frequency plane. Each RDF is associated with a specific filter that has been optimized for the specific feature. The filters are preferably composed of nonlinear functions with a preset number of parameters but it is clear that other types of composites may be also used.

According to one preferred embodiment one sub-method (RDF1) is optimal for a steady condition. According to another preferred embodiment at least one sub-method (RDF2) comprises determination of temporal changes in the respiratory frequencies by defining temporal deviations in the distribution of frequencies. According to another preferred embodiment one or more sub-methods (RDFi) are controlled dynamically according to the heart rate period. Heart beat level based weighting or heart beat level based conditional functions are possible. In a simple embodiment the system chooses a certain sub-method from two or more sub-methods according to the heart rate period.

Usually all sub-methods are based on heart rate variability, but in a simple system one can be based directly on heart rate period.

A sub-method also may be based on time domain indices. Examples are:
1) A curve fitting approach with linear or polynomical equations, and
2) A peak-to-low information, wherein peaks and lows in the heart beat oscillations are detected using a mathematical function, such as gradient change, or local maximum.

The time-frequency distribution of the HRV have several important respiratory period associated features that may have to be taken into account. It is important to design the features and composition of features in terms of mathematical and physiological models that overlap as much as possible. In another words, an understanding of the physiological properties of the traces of respiratory activity on HRV is essential in the design of mathematically derived features.

A useful feature may be successful in mapping some of the following properties in the time-frequency plane of the R-R signal. The amplitude of the RSA is an important characteristic, since RSA is often associated with a peak power in the spectrum or time-frequency map. This may be obtained by deriving the upper gradients or local maximums along the frequency dimension of the time-frequency transformed R-R series. The instantaneous center frequency of the spectrum may provide important information on the center of the mass properties of the spectrum and thus may be more robust to the overall changes in the frequency location of the respiratory signal. Another important property that is required to be covered is the fact that dynamic changes in the respiratory period are often associated with a sudden change in the frequency and time location of the power, that is, a certain location in the time-frequency map of the R-R series shows an instantaneous increase in the RSA power. In principle, it is possible to sensitize different and also similar types of features into a certain (respiratory) frequency range using them on a frequency-restricted form. This may be necessary, for example, to the detection of low-frequency periods in the respiration that are often single deviations from a higher mean respiratory frequency.

Figure 8:
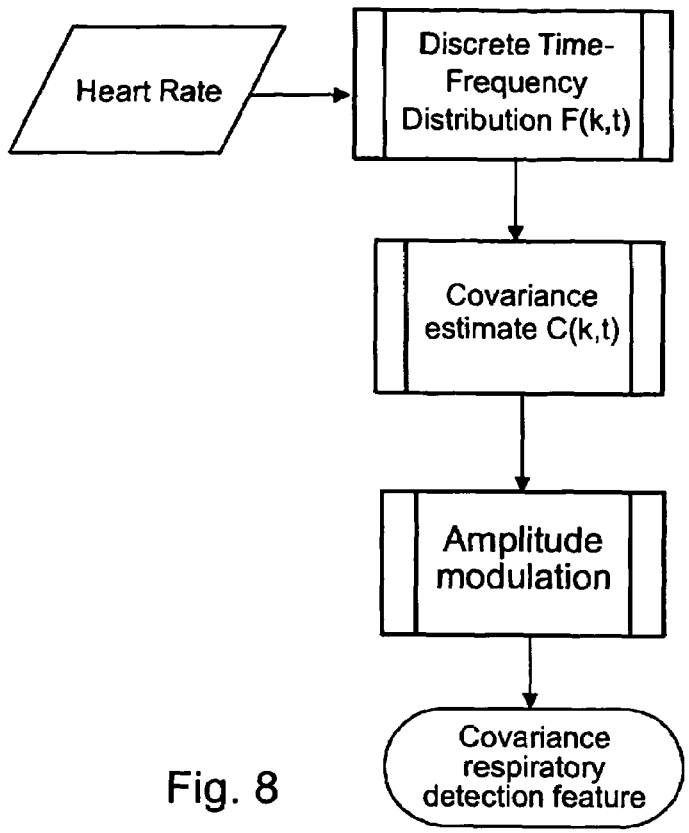
FIG. 8 presents the procedure for extracting a covariance estimate of dynamic HRV changes in the time-frequency plane.

The joint time-frequency covariance may be regarded as a two-dimensional filter that aims to detect dynamic changes in the time-frequency plane of the HRV within both time and frequency dimensions (see FIG. 8). The covariance term is a product of increased power within time and frequency planes as a function of difference to surrounding values. Thus, the covariance is able to capture dynamic changes in the respiratory period as a function of time-frequency coupled increase in HRV power at certain time and period.

$$F(k, t) = \sum_{n=-\infty}^{\infty} x(k+n) \cdot h_N(n) \cdot e^{-iwn} \qquad \text{Equation 1}$$

$$CF_1(k, t) = \frac{F(k, t)}{\sum_{n=1}^{N} F(k, n) \cdot h_{N'}(n)} \qquad \text{Equation 2}$$

$$CF_2(k, t) = \frac{F(k, t)}{\sum_{m=1}^{M} F(m, t)} \qquad \text{Equation 3}$$

$$C_1(k, t) = F(k, t)^{1+\log(1+CF_1(k,t))} \qquad \text{Equation 4}$$

$$C_2(k, t) = F(k, t) + F(k, t)^{\log(1+CF_1(k,t))} \qquad \text{Equation 5}$$

-continued $$C_3(k, t) = \exp(A(k) + \log(CF_2(k, t) + 1)) \cdot (B(k) + \log(CF_1(k, t) + 1))$$

Equation 6

Equation 1 presents the calculation of short-time Fourier transform calculated with an averaging window $h_N(n)$ with N nonzero values. Equations 4-6 illustrates different formulas for the covariance estimate.

In a similar manner to the amplitude modulation of the time-frequency plane, each respiratory detection feature may be associated with different window sizes in both frequency and time dimensions. Thus, the features may be composed of similar features but having different window sizes and amplitude modulation characteristics.

The respiratory detection feature combining expert function combines the information on the different features with their known reliabilities across frequencies. There are different types of expert functions. One expert function is based on a geometric mean of the feature estimates that have been weighted by a vector that contains the reliability of each respiratory detection feature across different frequencies.

$$y(t) = \frac{\sum_{j=1}^{n} f_j(t) \cdot g_j(f_j(t))}{\sum_{j=1}^{n} g_j(f_j(t))}$$

Equation 1 where $y(t)$ denotes the result estimate, $f_j(t)$ denotes an estimate of the sub-method j and $g_j(f_j(t))$ denotes a weighting factor.

Figure 9:
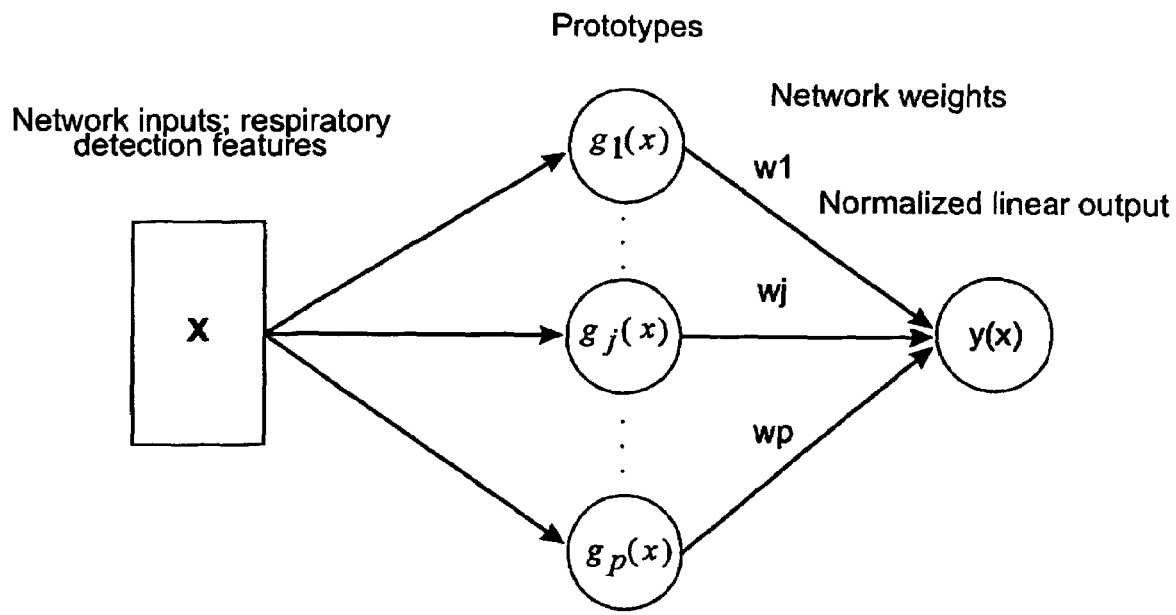
FIG. 9 shows detailed information on an analysis of respiratory detection features using a supervised learning neural network based expert function.

FIG. 9 shows a stochastic neural network based expert function that is based on a supervised learning radial based neural network. The neural network combines the respiratory detection features in the network that fires the node of prototypical respiratory frequency based on the multidimensional distribution of all respiratory detection features. Both of these methods provide both the respiratory frequency and the reliability of the estimated respiratory frequency.

The neural network is a radial basis network where each unit $g_j(x)$ gives a firing intensity with an Euclidian distance between the prototype μ and network input x (see equations 8a and 8b). The overall network output is a sum of the bias term b and the normalized linear output of the network units and weights.

$$y(x) = \frac{\sum_{j=1}^{p} w_j \cdot g_j(x)}{\sum_{j=1}^{p} g_j(x)} + b$$

Equation 8a $$g_j(x) = \exp\left(-\frac{\|x - \mu_j\|^2}{2\sigma_j^2}\right)$$

Equation 8b

It is important to notice that the essential characteristics of the expert function combining respiratory detection features are defined in terms of capacity to learn to combine features on the basis of empirical pre-determined data and on the combination of different features to provide a single estimate of the respiration. Thus, it is clear that, apart from the examples shown here, the expert function can be based on different mathematical functions, such as other types of neural network implementations, non-linear models, fuzzy systems, time series models, and other types of multivariate models capable of transferring and combining the information from several inputs into one estimate. In specific, it is clear that the deterministic model shown here is merely an example of an implementation of such combinatory function.

$$rb_1(t) = \sum_{j=1}^{p} g_j(x(t))$$

Equation 9

$$rb_2(t) = \frac{\sum_{j=1}^{p} g_j(x(t)) \cdot (w_j - y(x(t)))^2}{\sum_{j=1}^{p} g_j(x(t))}$$

Equation 10

$$rb_3(t) = \frac{\sum_{j=1}^{n} g_j(f_j(t)) \cdot (y(t) - f_j(t))}{\sum_{j=1}^{n} g_j(f_j(t))}$$

Equation 11

In the radial based neural network implementation, the reliability of the respiratory period signal may be calculated from the firing intensity $g_j(x(t))$ of each network prototype as presented in equation 9. Alternative way would be to calculate weighted standard deviation of the network weights $w_j$ and network output $y(x(t))$, where firing intensity is used as a weighting factor (equation 10). Also reliability of the deterministic expert function may be calculated with a weighted standard deviation of the features $f_j(t)$ and function output $y(t)$ (see equation 11). The deterministic expert function is presented in FIG. 9. The weights used to modify respiratory detection features are used as a weight for the reliability estimate. In both cases weighted standard deviation describes the agreement between the features affecting the result most, e.g. the features having great weighting factor. The more disagreement or deviation the less reliable the respiration frequency estimator is.

The reliability may be used independently as a marker of cardio respiratory coupling i.e. the extent of which cardiac and respiratory rhythms are coherent. This correlates with the level of physiological stability and stress.

The reliability information is used to perform a time-domain correction of the respiratory estimate. This correction uses the available information on respiratory frequency, the required time interval for such respiratory cycle, and reliability estimate to determine a least-cost pathway to the respiratory frequency. The respiratory frequency is then transformed to respiratory period and respiratory rate (cycles/minute). The respiratory information may be further averaged using, e.g., a Hanning window. This procedure may be performed in an adaptive manner that takes an advantage of the reliability information by minimizing the weight of potentially unreliable respiration segments on the end-measure of respiratory period.

$$yc(t) = \frac{\sum_{j=-\infty}^{\infty} h_N(j) \cdot rb(j) \cdot y(j)}{\sum_{j=-\infty}^{\infty} h_N(j) \cdot rb(j)}$$

Equation 12

An example of a simple correction formula is given by equation 12. The variable $h_N(j)$ presents an averaging window, e.g. Hanning window, centered at time t with N nonzero values and rb(j) is the reliability estimate of the respiration estimate y(j).

The invention also can be utilized in implementations using one fixed sub-method, when this is chosen from several sub-methods by an expert function and which are tested with empirical data. The choice of the sub-method can be based on criteria of the targeted use. Thus, one skilled in the art can seek an optimum sub-method for steady or exercise condition, etc.

The whole procedure for deriving reliable information on respiratory activity from heart rate data will be illustrated with FIGS. 11-17.

Figure 11A:
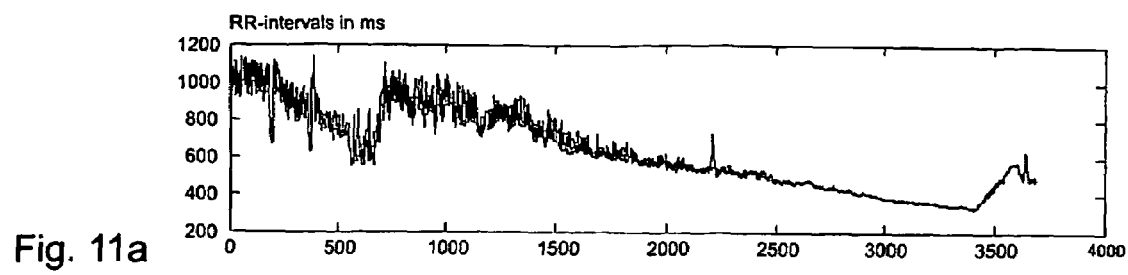
FIG. 11a presents the original RR-interval time series of the analysis.
Figure 11B:
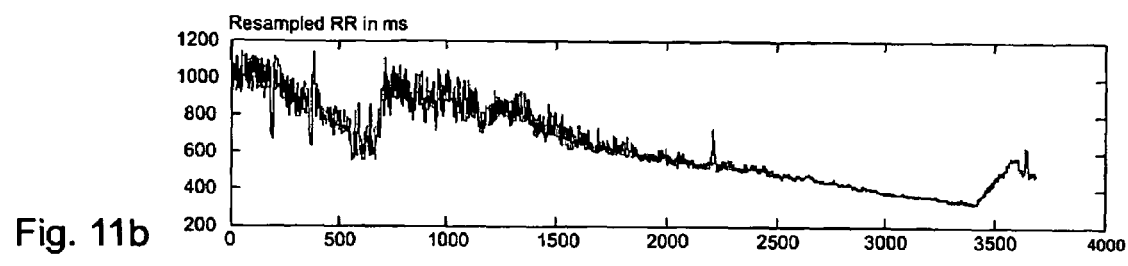
FIG. 11b illustrates the corresponding five hertz resampled RR.
Figure 11C:
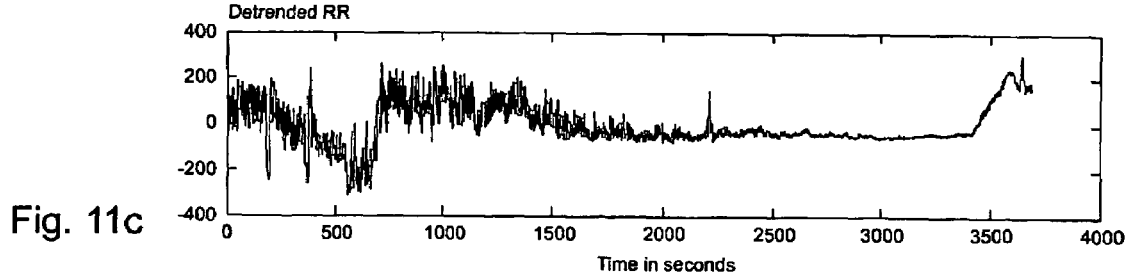
FIG. 11c presents its detrended counterpart.

FIGS. 11a, 11b and 11c present heart rate raw data, filtered data and detrended data, which will be the base for the next step. Time series present different features that will be exploited in the steps demonstrated in FIGS. 12-17. Each FIR filter is set to cut off frequencies below 0.1 Hz and frequencies above 1.5 Hz. The first and third FIR-filters both have five hundred parameters while feature one has thirty. The latter results in less sharp cut off in the lower frequency bound, allowing frequencies less than 0.1 Hz to appear in the resulting time series, but with smaller amplitude.

Figure 12A:
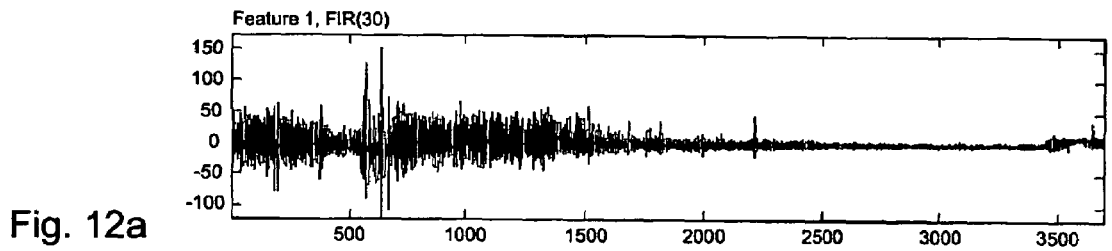
FIGS. 12a, 12b and 12c demonstrate three different time series result to a FIR-digital filtering applied to detrended and resampled RR time series presented in FIG. 11c.
Figure 12B:
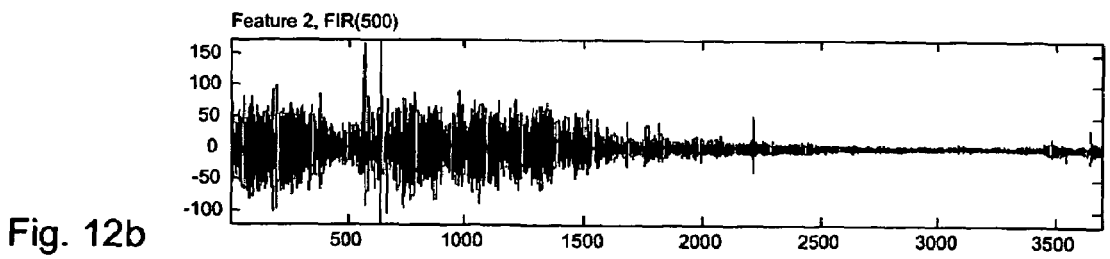
Figure 12C:
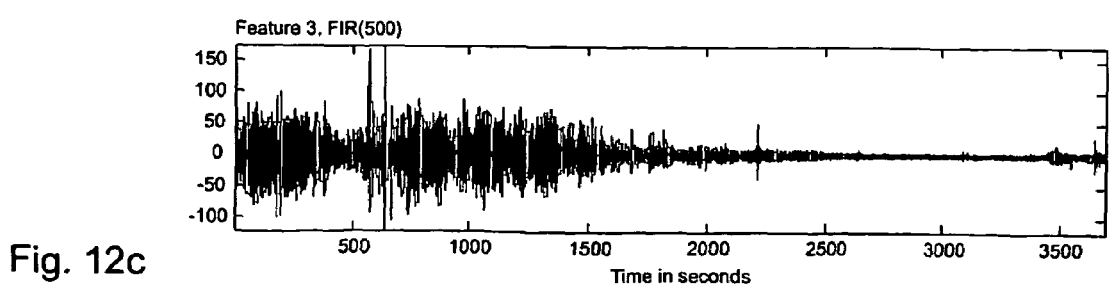

FIGS. 12a, 12b and 12c present different filtering of data. All three time-frequency distributions are calculated with a short-time Fourier transformation applied to 201 points, i.e. 20 seconds, Hanning window defining the time-resolution of the time-frequency distribution. The time-frequency covariance defined in equations 2 and 4 of FIG. 8 is applied for the second feature with 51 points Hanning window (i.e. 10 seconds). The joint time-frequency covariance may be regarded as a two-dimensional filter that aims to detect dynamic changes in the time-frequency plane of the HRV within both time and frequency dimensions.

Each feature signal demonstrated in FIGS. 12a, 12b and 12c is transformed to a discrete time-frequency presentation illustrating the frequency-power-contents of the time series. All three time-frequency distributions are calculated with a short-time Fourier transformation applied to 201 points, i.e. 20 seconds, Hanning window defining the time-resolution of the time-frequency distribution. The time-frequency covariance defined in equations 2 and 4 of FIG. 8 is applied for the second feature with 51 points Hanning window (i.e. 10 seconds). The joint time-frequency covariance may be regarded as a two-dimensional filter that aims to detect dynamic changes in the time-frequency plane of the HRV within both time and frequency dimensions.

Figure 13A:
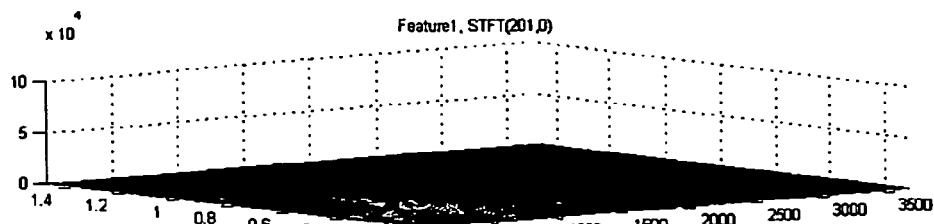
FIGS. 13a, 13b and 13c show presentations, where each feature signal demonstrated in FIGS. 12a-c is transformed to a discrete time-frequency presentation illustrating the frequency-power-contents of the time series.
Figure 13B:
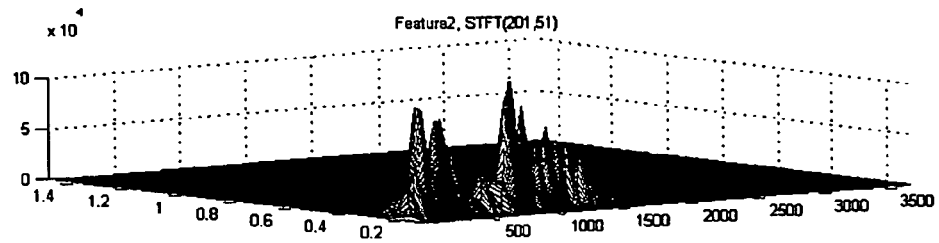
Figure 13C:
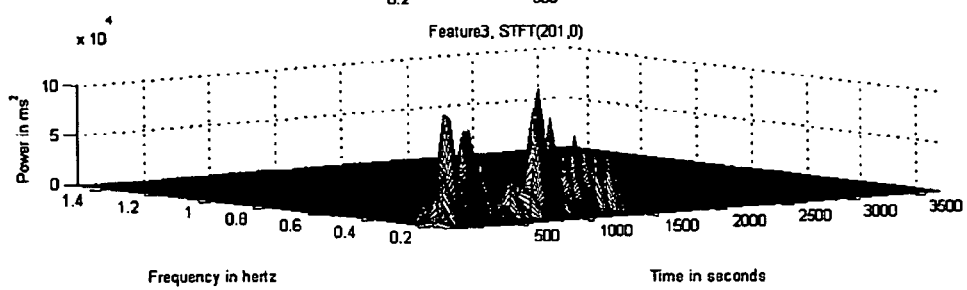
Figure 14:
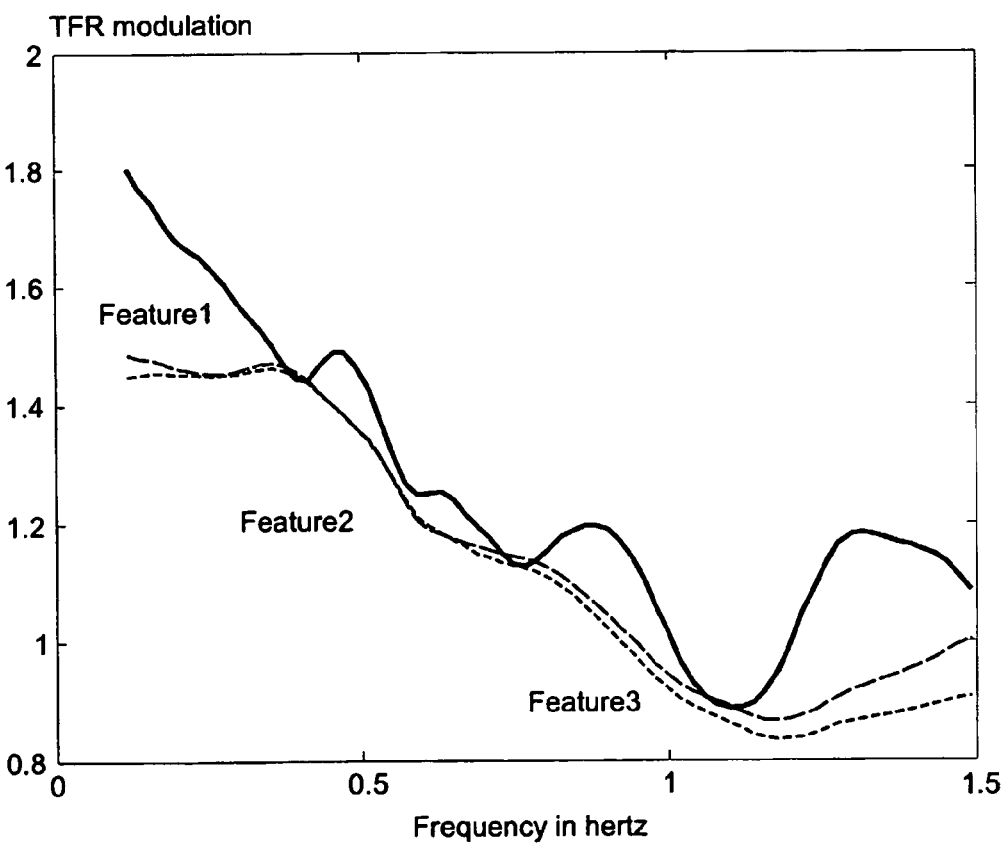
FIG. 14 demonstrates the custom-designed and optimized weighting factors that are used to modulate each time-frequency distribution presented in FIG. 13.

FIG. 14 demonstrates the custom-designed and optimized weighting factors that are used to modulate each time-frequency distribution presented in FIGS. 13a-c.

Figure 15A:
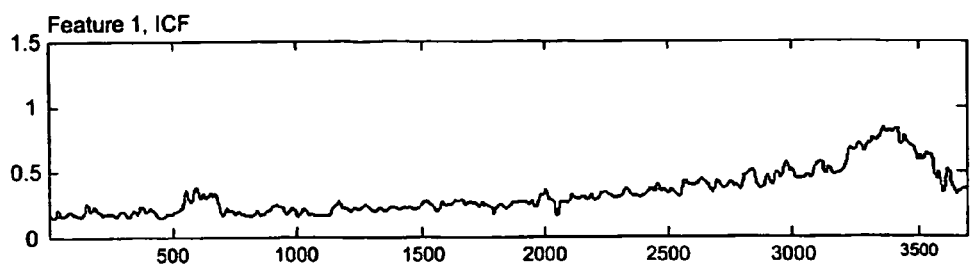
FIGS. 15a, 15b and 15c demonstrate the resulting frequency moments calculated from the modulated time-frequency distributions (see FIGS. 13a-c and 14).
Figure 15B:
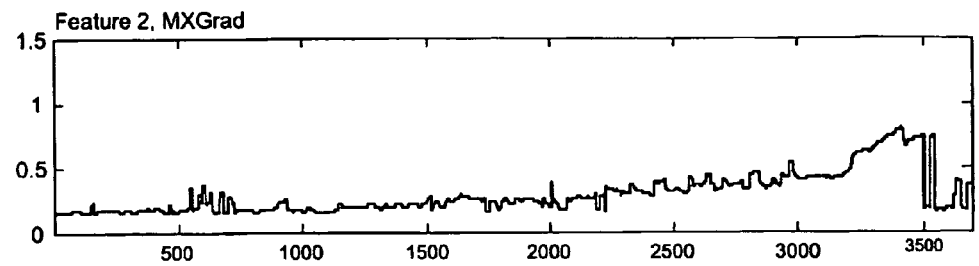
Figure 15C:
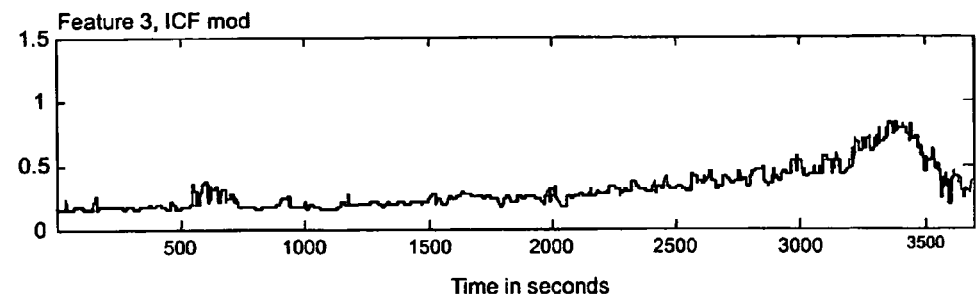

FIGS. 15a-c demonstrate the resulting frequency moments calculated from the modulated time-frequency distributions (see FIGS. 13a-c and 14). The first feature is calculated with instantaneous center frequency, the second with a maximum gradient approach and the third with an instantaneous frequency with a selection of closest maximum gradient (i.e., change of the gradient sign in the amplitude distribution). Each feature presents an estimate of the respiration frequency for each time instant.

Figure 16:
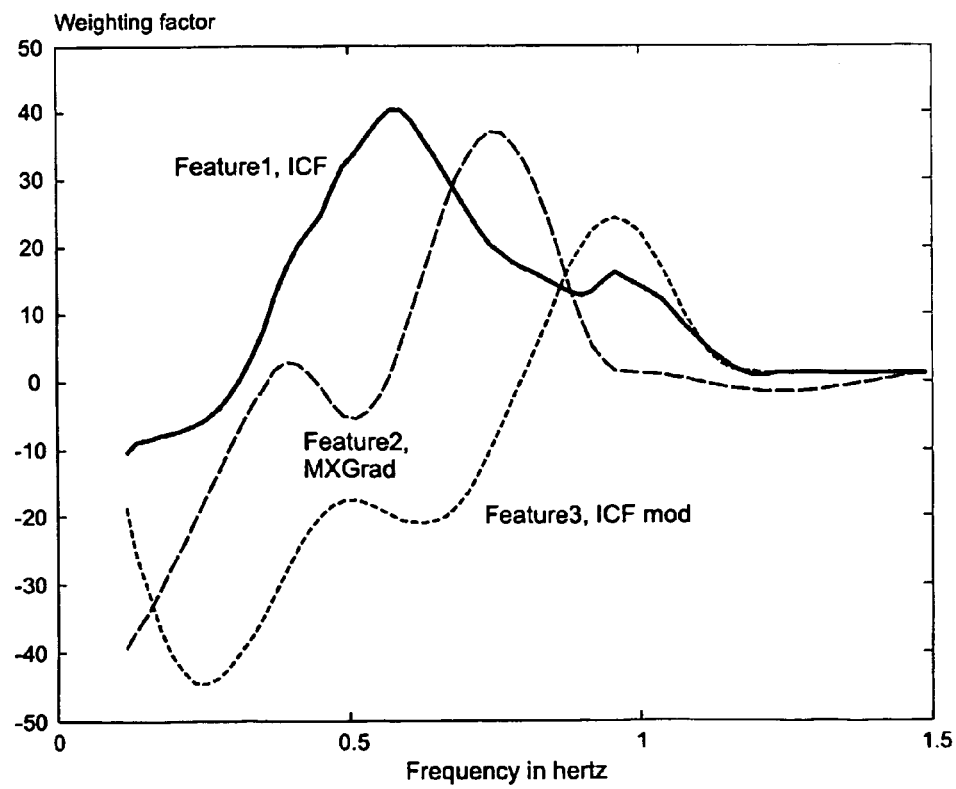
FIG. 16 shows the logarithmic reliability weightings of a deterministic expert function.

FIG. 16 shows the logarithmic reliability weightings of a deterministic expert function defined in equation 7. Each presented vector contains the reliability of each respiratory detection feature across different frequencies.

Figure 17A:
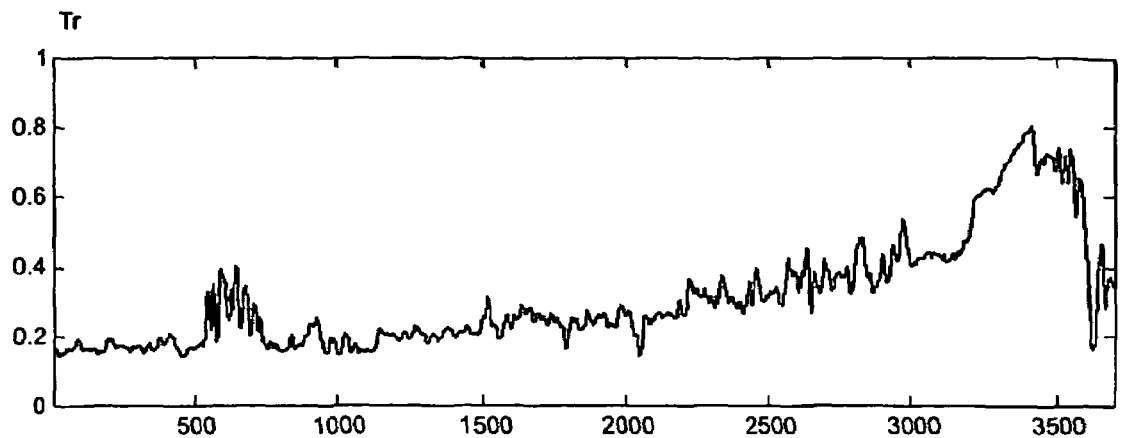
FIG. 17a demonstrates the true respiration frequency for each time instant measured with chest expansion.
Figure 17B:
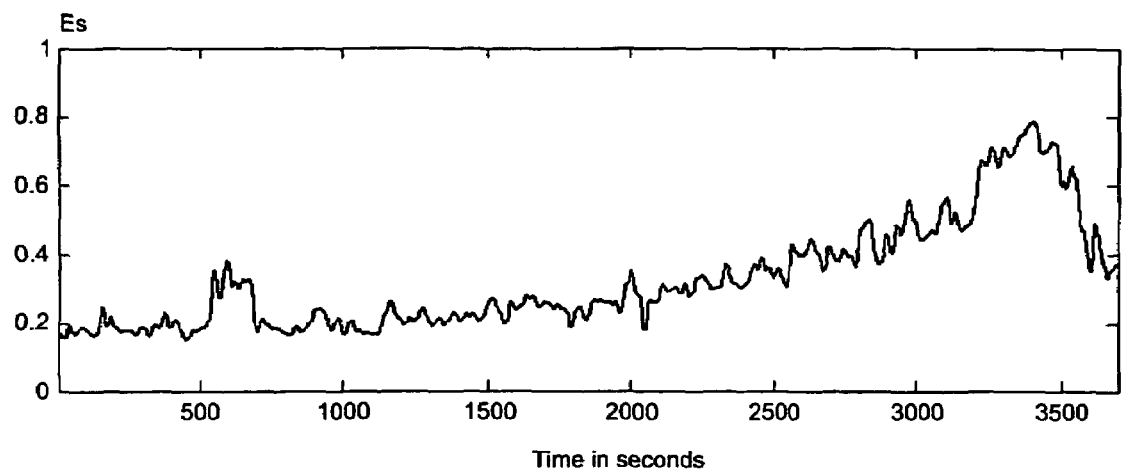
FIG. 17b presents the estimated respiration frequency, the result of the combination of three respiratory detection features joined with the formula of the expert function.

FIG. 17a demonstrates the true respiration frequency for each time instant measured with a chest expansion. The time series is moving averaged with a twenty seconds Hanning window. FIG. 17b presents the estimated respiration frequency, the result of the combination of three respiratory detection features joined with the formula illustrated in equation 7. The error of combined result is significantly smaller than that of each sub-method.

The estimate is averaged with a reliability weighted Hanning window of twenty seconds. The reliability correction is defined with equations 11 and 12. The estimate was achieved from a pure RR-interval time series transformed with several steps to respiratory detection features. The required steps are demonstrated in FIGS. 11-17. The model error was smallest when all three respiratory detection features were utilized. Generally the error of combined result is always significantly smaller than that of each sub-method.

Figure 10A:
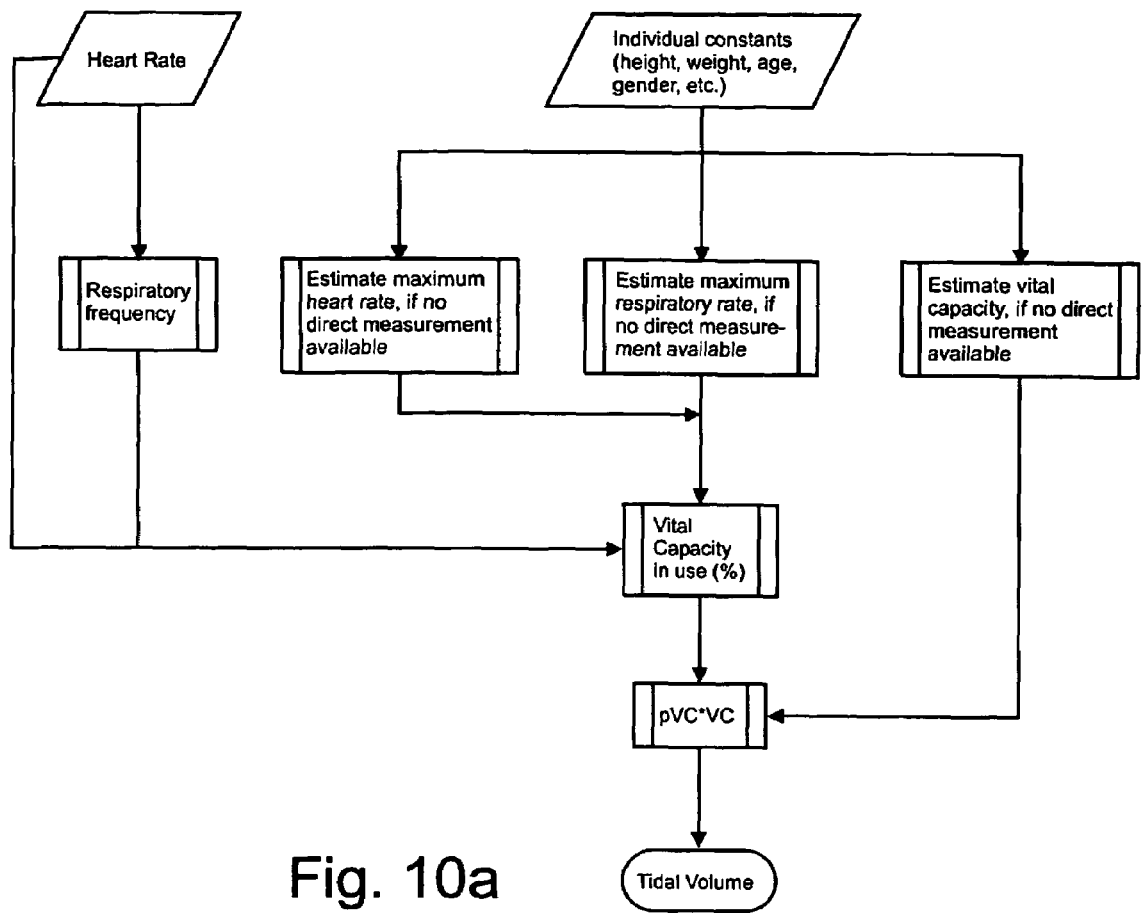
FIGS. 10a and 10b illustrate the computation of tidal volume and ventilation.
Figure 10B:
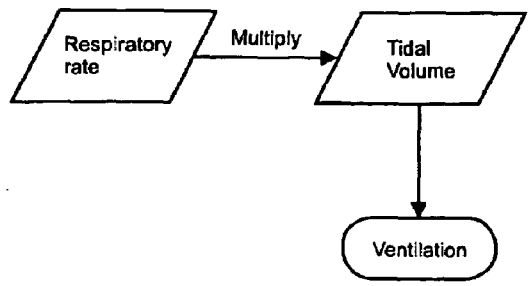

The computation of ventilation requires information on the tidal volume (see FIGS. 10a and 10b). An estimate of the tidal volume may be derived by utilizing different forms of information on the basis of the heart period signal. For example, the functional organization of the respiratory system has an impact on both respiratory period and tidal volume. Therefore, given the known relationships between the respiratory period and tidal volume during and transitions to different states, the information inherent in the heart period derived respiratory frequency may be used in providing values of tidal volume. Specifically, the tidal volume contains inherent dynamics which may be, after modeling, applied to more closely capture the behavioral dynamics of the tidal volume. Moreover, it appears that the heart period signal itself is closely associated with tidal volume and therefore may be used to increase the reliability of deriving information on tidal volume.

The accuracy of the tidal volume estimation may be further enhanced by using information on the subject's vital capacity (i.e., the maximal quantity of air that can be contained in the lungs during one breath). The information on vital capacity, as based on physiological measurement or on estimates derived from body measures such as height and weight, may be helpful in estimating tidal volume, since it is likely to reduce the effects of individual differences on the estimated tidal volume. Using information on the vital capacity, the mathematical model may first give values on the percentage of lung capacity in use, which may be then transformed to liters per breath as follows:

Tidal volume (liters/breath)=proportion of lung capacity in use (% of vital capacity)*vital capacity (liters)

Different sources of information, that is, frequency of respiration, heart rate level, vital capacity, and heart rate variability changes associated with tidal volume, must be combined using an algorithm that integrates information from several sources to provide an estimate of the tidal volume. This task may be performed preferentially by neural network based transfer function, multidimensional polynomial or other nonlinear model, a fuzzy system based structure or other multivariate method capable of providing one estimate from several inputs. The estimate may be further enhanced with a use of percentage of maximum values in the inputs or output of the estimation function. The maximum values may be measured or estimated based on subject characteristics such as age, height, weight, and age.

Despite the selection of the actual method that is used the present embodiment, it should be clear to one experienced in the art that, to perform this task, the common feature of the task is the optimizing of tidal volume estimation based on, for example, least squares or other type of fit between the features and actual tidal volume. It is therefore clear that the selection of the combinatory method must be based on true physiological law-like relationships between different components and may be performed with different types of methods within the scope of the present embodiments.

Finally, the minute ventilation may be derived by multiplying respiratory rate (breaths/min) with tidal volume (liters/breath). It should be clear to one familiar with the art that the exact formulation of the preferred embodiments of deriving information on ventilation via tidal volume does not necessarily involve all these steps and may comprise, for example, a direct use of heart period and respiratory period information on the estimation of ventilation volume using a multivariate mathematical model, such as, for example, a neural network function.

Implementations of the invention can be a computer software in a personal computer, a heart rate monitor (wrist top computer) and an ergometer (a stationary bicycle) or other fitness exercise equipment. The estimation can be applied to determine oxygen or caloric consumption, or threshold values for energy metabolism.

It is apparent to anyone skilled in the art that the invention is not restricted to the embodiments shown as examples but can vary considerably within the scope of the claims presented below.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A method for deriving reliable information on respiratory activity from a pattern of rhythmic changes in heart beat data, the method comprising the steps of:
    measuring an electrocardiographic (ECG)-signal;
    obtaining RR-interval data from the ECG-signal;
    calculating respiratory frequency estimates from the RR-interval data using two or more sub-methods, at least one sub-method being based on heart rate variability;
    combining the calculated respiratory frequency estimates in a health apparatus using an expert function including a weight vector across frequencies for each frequency estimate and obtaining a resulting respiratory frequency estimate directly in the combination made by said expert function.

2. Method according to claim 1, characterized in that one sub-method is optimal for a steady condition.

3. Method according to claim 1, characterized in that at least one sub-method comprises determination of temporal changes in the respiratory frequencies by defining temporal deviations in the distribution of frequencies.

4. Method according to claim 1, characterized in that post-correction of the respiratory period is made with a chosen method.

5. Method according to claim 1, characterized in that an expert function comprises a reliability weightings for each sub-method as a function of the calculated respiratory frequency by the respective sub-method.

6. Method according to claim 1, characterized in that at least one sub-method is controlled dynamically according to the heart rate level.

7. Method according to claim 1, characterized in that the expert function makes a pre-selection from several different sub-methods with pre-selected criteria.

8. Method according to claim 7, characterized in that the expert function makes a fixed pre-selection for an implementation according to pre-measured empirical data.

9. Method according to claim 1, characterized in that information on tidal volume is calculated using information on RR-interval data.

10. Method according to claim 9, characterized in that information on the ventilation from the heart beat data is derived wherein the following methods (a-c) are used:
    a. Multiplying heart beat derived values of tidal volume with heart beat derived values on the frequency of breathing,
    b. Applying information on at least one chosen parameter derived from the heart beat,
    c. Using a mathematical function to transfer the chosen parameters measures into information on ventilation.

11. Method according to claim 1, characterized in that the method is used in a wearable computer.

12. Method according to claim 1, characterized in that the method is used in a fitness exercise equipment.

13. Method according to claim 1, characterized in that the reliability of the estimate is determined and expressed with the estimate.

14. Method according to claim 1, characterized in that the resulting respiratory frequency is used to determine oxygen consumption.

15. Method according to claim 1, characterized in that the resulting respirator frequency is used to determine caloric consumption.

16. Method according to claim 1, characterized in that the resulting respiratory frequency is used to determine threshold values for energy metabolism.

* * * * *